(12) United States Patent
Yamashita et al.

(10) Patent No.: US 7,780,605 B2
(45) Date of Patent: Aug. 24, 2010

(54) BLOOD PRESSURE MEASURING APPARATUS ENABLING ACCURATE BLOOD PRESSURE MEASUREMENT

(75) Inventors: Shingo Yamashita, Kyoto (JP); Akihisa Takahashi, Kyoto (JP); Yoshihiko Sano, Kyoto (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 0 days.

(21) Appl. No.: 12/084,981

(22) PCT Filed: Oct. 18, 2006

(86) PCT No.: PCT/JP2006/320699

§ 371 (c)(1),
(2), (4) Date: May 14, 2008

(87) PCT Pub. No.: WO2007/063650

PCT Pub. Date: Jun. 7, 2007

(65) Prior Publication Data

US 2009/0124913 A1 May 14, 2009

(30) Foreign Application Priority Data

Nov. 30, 2005 (JP) .............................. 2005-346344

(51) Int. Cl.
A61B 5/02 (2006.01)

(52) U.S. Cl. ........................ 600/490; 600/485; 600/487; 600/499; 600/492

(58) Field of Classification Search ................. 600/499, 600/488, 490, 492
See application file for complete search history.

(56) References Cited

U.S. PATENT DOCUMENTS 4,572,205 A 2/1986 Sjonell

2005/0171443 A1 8/2005 Gorenberg et al.
2005/0182332 A1* 8/2005 Sano et al. ................. 600/499

FOREIGN PATENT DOCUMENTS

| CN | 1657002 | 8/2005 |
|---|---|---|
| EP | 1256313 | 11/2002 |
| EP | 1591061 | 11/2005 |
| JP | 60-92737 | 5/1985 |
| JP | 3-280931 | 12/1991 |
| JP | 4-338450 | 11/1992 |
| JP | 2004-174029 | 6/2004 |
| JP | 2005-230175 | 9/2005 |
| RU | 2 281 687 | 8/2006 |

OTHER PUBLICATIONS

International Search report mailed Nov. 14, 2006, directed to counterpart International Application No. PCT/JP2006/320699. 4 pages.
Russian Office Action mailed on Oct. 18, 2009 directed at patent application No. 2008126205; 12 pages.
Russian Office Action mailed on Sep. 18, 2009 directed at patent application No. 2008126205; 12 pages.
Shahov et al., 2003. p. 18-29.
Shahov et al., 2003. p. 30-37.
European Supplementary Search report mailed on Nov. 18, 2009 directed at application No. 06811938.7-2319; 4 pages.
Chinese Office Action mailed Jan. 8, 2010, directed to counterpart Chinese Patent Application No. 200680045062.8; 9 pages.

* cited by examiner

*Primary Examiner*—Robert L Nasser
*Assistant Examiner*—Michael D'Angelo
(74) *Attorney, Agent, or Firm*—Morrison & Foerster LLP

(57) ABSTRACT

A blood pressure measuring apparatus includes a plurality of mechanisms compressing a cuff, and the mechanisms are separately controlled. Therefore, a stable measurement attitude is maintained irrespective of a circumference or a shape of an upper arm. Compression degrees are separately controlled, whereby a pressure can evenly be applied to the cuff to improve a compression force acting on an artery.

12 Claims, 14 Drawing Sheets

MEASURING FLUID BLADDER
WINDING PART

MEASURING FLUID BLADDER
WINDING PART

BLOOD PRESSURE MEASURING APPARATUS ENABLING ACCURATE BLOOD PRESSURE MEASUREMENT

REFERENCE TO RELATED APPLICATIONS

This application is a national stage application under 35 USC 371 of International Application No. PCT/JP2006/320699, filed Oct. 18, 2006, which claims the benefit of Japanese Application No. 2005-346344, filed Nov. 30, 2005, the contents of which are incorporated herein by reference.

TECHNICAL FIELD

The present invention relates to a blood pressure measuring apparatus, and particularly to a blood pressure measuring apparatus for measuring a blood pressure with a blood pressure measuring fluid bladder attached to a measurement region.

TECHNICAL FIELD

Conventionally there is a blood pressure measuring apparatus, wherein a cuff including a blood pressure measuring air bladder functioning as the blood pressure measuring fluid bladder is wound around and fixed to a part (for example, an upper arm) of a living body serving as the measurement region, and an internal pressure of the part of the living body by pressurizing and depressurizing the air bladder, thereby measuring the blood pressure.

In the blood pressure measuring apparatus having the above-described configuration, when the cuff is not properly wound, a lack of compression of the blood pressure measuring fluid bladder or an unstable measurement attitude cause a noise in a cuff pressure. This leads to deteriorate measurement accuracy of the blood pressure.

In the case where the blood pressure is measured in pressurizing the blood pressure measuring fluid bladder, a change in measurement attitude of a subject possibly deteriorates the measurement accuracy.

Therefore, it is necessary that the cuff be wound around various circumferences of the brachia of the subjects such that the measurement attitude is properly obtained.

As to a technique of winding the cuff, for example, Japanese Patent Laying-Open No. 2005-230175 (hereinafter, referred to as Patent Document 1) previously applied by the inventor discloses a living body compressing and fixing apparatus. The living body compressing and fixing apparatus disclosed in Patent Document 1, includes a compressing fluid bladder in an outer circumference of the blood pressure measuring fluid bladder while the blood pressure measuring fluid bladder is wound around the measurement region (upper arm), and the compressing fluid bladder is inflated to press the blood pressure measuring fluid bladder against the measurement region from the outer circumference with an even pressure in a circumferential direction and a length direction of the upper arm, thereby fixing the cuff to the measurement region.

FIGS. 13A and 13B are schematic views illustrating fixing of the measuring fluid bladder when the blood pressure is measured using the blood-pressure meter on which the living body compressing and fixing apparatus is mounted. Referring to FIG. 13A, the subject inserts the upper arm serving as the measurement region into a housing. The measuring fluid bladder and a winding part functioning as a fluid bladder are provided in the housing, and the housing is disposed at an angle at which the upper arm is easily inserted into the blood-pressure meter. When an instruction of measurement start is provided, as shown in FIG. 13B, a fluid is supplied to the winding part to inflate the winding part, and the measuring fluid bladder is pressed against the upper arm with the substantially even pressure in the circumferential direction and length direction of the upper arm.

Patent Document 1: Japanese Patent Laying-Open No. 2005-230175

DISCLOSURE OF THE INVENTION

Problems to be Solved by the Invention

However, in the mechanism of the living body compressing and fixing apparatus disclosed in Patent Document 1, because the measuring fluid bladder is pressed with substantially even pressure in the circumferential direction of the upper arm irrespective of the circumference of the upper arm serving as the measurement region, as shown in FIG. 13B, the measuring fluid bladder is largely inflated for a person having a small circumference of the upper arm, and sometimes an elbow is uplifted by an upward pressing force of the winding part. In such cases, unfortunately the upper arm is not fixed to the blood-pressure meter, and sometimes measurement result cannot correctly be obtained due to the unstable measurement attitude.

Additionally, in the mechanism of the living body compressing and fixing apparatus, the measuring fluid bladder is pressed with substantially even pressure in the length direction of the upper arm irrespective of the circumference of the upper arm serving as the measurement region. Therefore, for a person having a tapered shape upper arm, when the measuring fluid bladder is pressed based on a thick side of the tapered shape upper arm, sometimes the measuring fluid bladder is not properly pressed against a thin side of the tapered shape upper arm. When the measuring fluid bladder is pressed based on the thin side of the tapered shape upper arm in order to fix the measuring fluid bladder to the whole of the measurement region, sometimes the measuring fluid bladder is excessively pressed against the thin side of the tapered shape upper arm. In such cases, unfortunately the measuring fluid bladder is not properly pressed against the measurement region, and sometimes the correct measurement result cannot be obtained.

Additionally, in the mechanism of the living body compressing and fixing apparatus, as shown in FIG. 14, the measuring fluid bladder is inflated by supplying the fluid, and the living body is compressed from the outer circumference of the by the measuring fluid bladder (air bladder) whose section becomes a circular or oval shape due to the inflation through a plane formed by a flexible member such as a curler. Therefore, sometimes the pressing force of the winding part does not act on the a portion away from the center of the measuring fluid bladder depending on the sectional shape of the measuring fluid bladder and the shape of the flexible member facing the measuring fluid bladder. In such cases, as shown in FIG. 14, sometimes the measuring fluid bladder is not pressed against the artery over the necessary range, which results in a problem in that the correct measurement result is not obtained.

In view of the foregoing, an object of the present invention is to provide a blood pressure measuring apparatus properly compressing the measuring fluid bladder against the measurement region.

Means for Solving the Problems

In accordance with an aspect of the present invention, a blood pressure measuring apparatus includes a measuring fluid bladder corresponding to a measuring air bladder 13; a first supply part corresponding to a pump 21, a valve 22, a pump driving circuit 26, and a valve driving circuit 27 to supply a fluid to the measuring fluid bladder; a sensor corresponding to a pressure sensor 23 to measure an internal pressure of the measuring fluid bladder; a measuring fluid bladder compressing part corresponding to a compressing and fixing air bladder 8 and a wire 81 to compress the measuring fluid bladder in a measurement region direction; and a compression degree detector corresponding to a pressure sensor 33 to measure a degree of the measuring fluid bladder compressed by the measuring fluid bladder compressing part, wherein the measuring fluid bladder compressing part includes a first compressing part to compress the measuring fluid bladder while exerting a first compression behavior; and a second compressing part to compress the measuring fluid bladder while exerting a second compression behavior.

Preferably, the blood pressure measuring apparatus further includes a controller corresponding to a CPU (Central Processing Unit) 40 to control compression of the measuring fluid bladder in the measuring fluid bladder compressing part, wherein the controller controls such that the first compressing part is compressed using the measuring fluid bladder while exerting the first compression behavior, and the controller controls such that the second compressing part is compressed using the measuring fluid bladder while exerting the second compression behavior.

In detail, the controller preferably controls compression in the measuring fluid bladder compressing part based on an internal pressure of the measuring fluid bladder, information indicating a change in internal pressure of the measuring fluid bladder, and the compression degree of the measuring fluid bladder compressing part.

Specifically, it is preferable that the measuring fluid bladder compressing part is a compressing fluid bladder, that the blood pressure measuring apparatus further includes a second supply part to supply a fluid to a first compressing fluid bladder functioning as the first compressing part; and a third supply part to supply a fluid to a second compressing fluid bladder functioning as the second compressing part, and that the controller controls fluid supply in the second supply part and the third supply part to control compression in the measuring fluid bladder compressing part.

Specifically, it is preferable that the measurement region is an upper arm, that the first compressing part and the second compressing part are disposed orthogonal to an artery of the upper arm with the measuring fluid bladder attached to the upper arm, wherein the first compressing part is disposed at a position where the measuring fluid bladder located above the upper arm is compressed from above toward the upper arm while the second compressing part is disposed at a position where the measuring fluid bladder located below the upper arm is compressed from below toward the upper arm, and that the controller performs control such that the first compressing part compresses the measuring fluid bladder and then the second compressing part compresses the measuring fluid bladder.

Alternatively, it is preferable that the measurement region is an upper arm, and that the first compressing part and the second compressing part are disposed in parallel with an artery of the upper arm with the measuring fluid bladder attached to the upper arm, wherein the first compressing part is disposed at a position close to a shoulder on an upstream side of the upper arm while the second compressing part is disposed at a position close to a wrist on a downstream side of the upper arm.

Preferably, the controller performs control such that a compression degree in the second compressing part is larger than a compression degree in the first compressing part.

Alternatively, it is preferable that the measurement region is an upper arm, and that the first compressing part and the second compressing part are disposed in parallel with an artery of the upper arm with the measuring fluid bladder attached to the upper arm, wherein the first compressing part is disposed in a substantial center in a direction parallel to the artery of the measuring fluid bladder while the second compressing part is disposed at a position closer to an end rather than the center in the direction parallel to the artery of the measuring fluid bladder, and that the controller performs control such that a compression degree in the second compressing part is larger than a compression degree in the first compressing part.

Alternatively, it is preferable the first compressing part is a part according to a first characteristic in the measuring fluid bladder compressing part and the first compressing part exerts the first compression behavior according to the first characteristic, while the second compressing part is a part according to a second characteristic in the measuring fluid bladder compressing part and the second compressing part exerts the second compression behavior according to the second characteristic.

In detail, it is preferable that the measuring fluid bladder compressing part is a compressing fluid bladder, and that the first characteristic and the second characteristic depend on the number of seams of the compressing fluid bladder.

Effects of the Invention

The blood pressure measuring apparatus according the present invention includes measuring fluid bladder compressing means for compressing the measuring fluid bladder corresponding to the cuff to press the measuring fluid bladder against the measurement region, the measuring fluid bladder compressing means having a plurality of compression behaviors, and the measuring fluid bladder compressing means compresses the measuring fluid bladder with different compression behaviors in the direction orthogonal to and/or parallel to the artery of the measurement region. Therefore, the unstable measurement attitude caused by the uplift of the measurement region can be prevented in compressing the measuring fluid bladder. The measuring fluid bladder can properly be fixed according to the shape of the measurement region such as the tapered shape. The measuring fluid bladder to which the fluid is supplied can properly be compressed over the necessary range, and the artery can properly be pressed. Accordingly, the measurement accuracy can be enhanced.

DESCRIPTION OF THE REFERENCE SIGNS 1 blood-pressure meter, 2 main body, 3 manipulation part, 4 display, 5 measuring part, 6 housing, 7 cover, 13 measuring air bladder, 10 curler, 8 and 8A to 8C compressing and fixing air bladder, 20 measuring air system, 23, 33A, and 33B pressure sensor, 21, 31A, and 31B pump, 22, 32A, and 32B valve, 26, 36A, and 36B pump driving circuit, 27, 37A, and 37B valve driving circuit, 28, 38A, and 38B amplifier, 29, 39A, and 39B A/D converter, 30A and 30B compressing and fixing air system, 40 CPU, 41 memory, 81 wire, 82 wire wind-up part, 100 upper arm

BEST MODES FOR CARRYING OUT THE INVENTION

Embodiments of the invention will be described below with reference to the drawings. In the following description, the same component and constituent are designated by the same numeral, and the same component and constituent have the same name and the same function.

Figure 1:
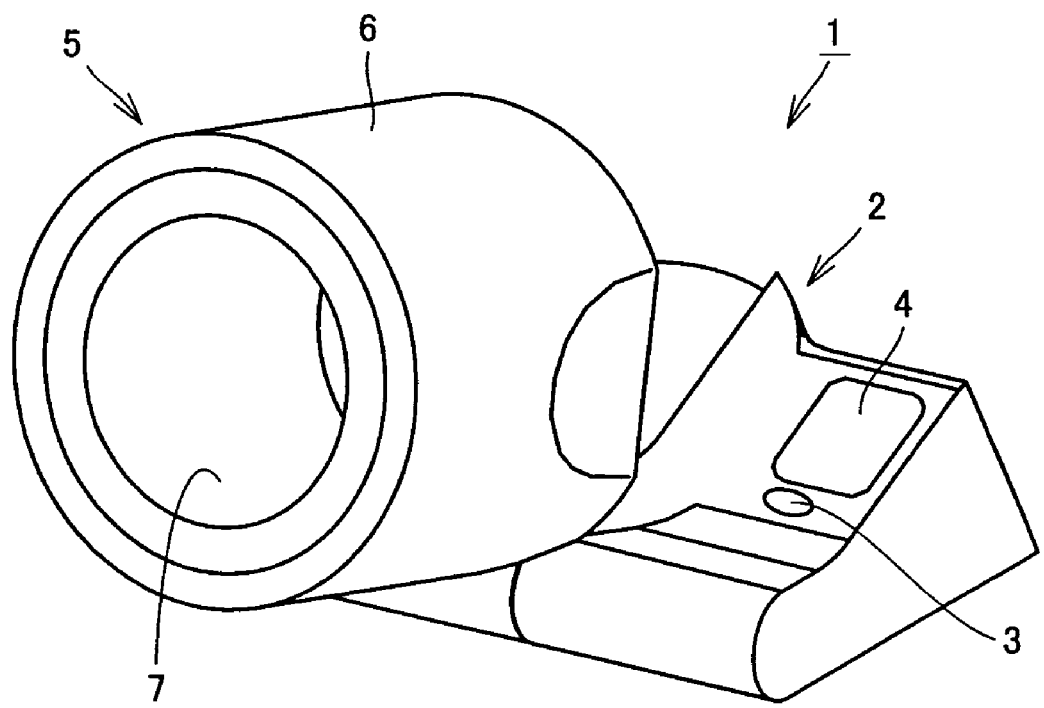
FIG. 1 is a perspective view showing a specific example of an appearance of a blood-pressure meter 1.

Referring to FIG. 1, a blood pressure measuring apparatus (hereinafter, referred to as blood-pressure meter) 1 according to the present embodiment mainly includes a main body 2 placed on a desk or the like, and a measuring part 5 for allowing an upper arm serving as a measurement region to be inserted thereinto. A manipulation part 3, a display 4, and an elbow holder are provided in an upper portion of main body 2. A power button and a measurement button are placed in manipulation part 3. Measuring part 5 is attached to main body 2 while an angle of measuring part 5 is variable with respect to main body 2, and measuring part 5 includes a housing 6 and a living body compressing and fixing apparatus. Housing 6 is a substantially cylindrical frame, and the living body compressing and fixing apparatus is accommodated in an inner circumferential portion of housing 6. As shown in FIG. 1, the living body compressing and fixing apparatus accommodated in the inner circumferential portion of housing 6 is not exposed in a normal usage state, but is covered with a cover 7.

First Embodiment

Figure 2:
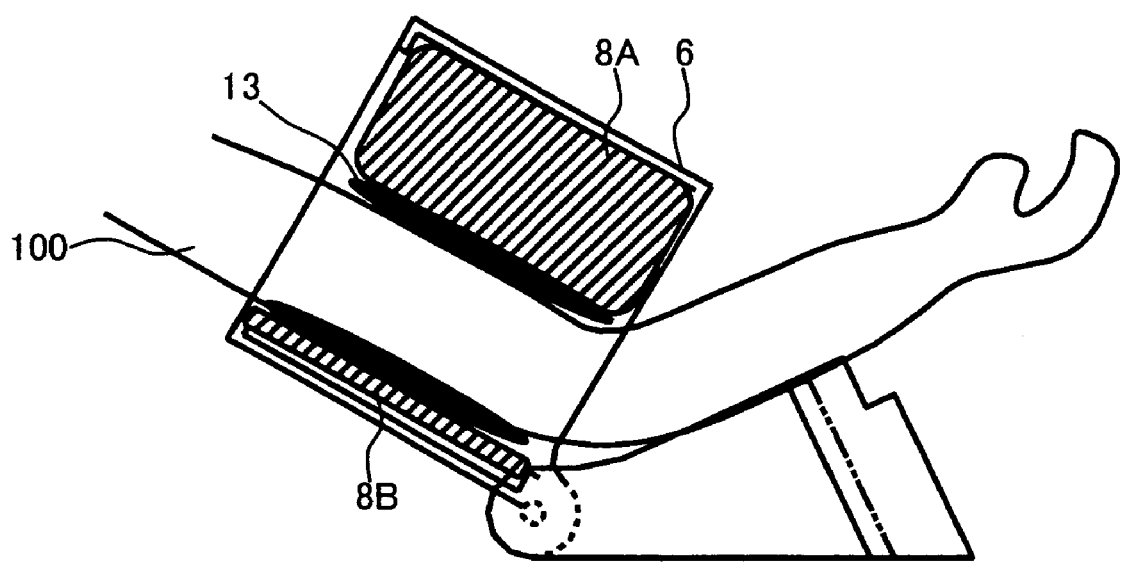
FIG. 2 is a schematic sectional view showing the blood-pressure meter 1 according to a first embodiment in measuring a blood pressure.

Referring to FIG. 2, in measuring the blood pressure, an upper arm 100 is inserted into housing 6 to place an elbow on the elbow holder, and an instruction is made to start measurement. Upper arm 100 is compressed and fixed by the living body compressing and fixing apparatus to measure the blood pressure.

The living body compressing and fixing apparatus includes a measuring air bladder 13, a curler 10 (see FIG. 3), and a compressing and fixing air bladder 8. Measuring air bladder 13 corresponding to the cuff is a measuring fluid bladder compresses the measurement region to measure the blood pressure. Curler 10 is the substantially cylindrical flexible member located outside measuring air bladder 13, and curler 10 can radially be expanded and compressed. Compressing and fixing air bladder 8 functioning as the measuring fluid bladder compressing means located outside curler 10, inflation of compressing and fixing air bladder 8 presses an outer circumferential surface of curler 10 toward the inside to reduce a diameter of curler 10, and compressing and fixing air bladder 8 compresses measuring air bladder 13 along with housing 6 through curler 10 to press measuring air bladder 13 against the measurement region of the living body.

In blood-pressure meter 1 according to the first embodiment, compressing and fixing air bladder 8 includes a plurality of compressing and fixing air bladders arranged in the circumferential direction of the upper arm orthogonal to the artery of the upper arm, and the compressing and fixing air bladders exert different compression behavior by separately controlling supply/discharge of air. At this point, specifically it is assumed that compressing and fixing air bladder 8 includes two compressing and fixing air bladders 8A and 8B. When the upper arm is inserted into housing 6, compressing and fixing air bladder 8A is disposed above the upper arm while compressing and fixing air bladder 8B is disposed below the upper arm.

Figure 3:
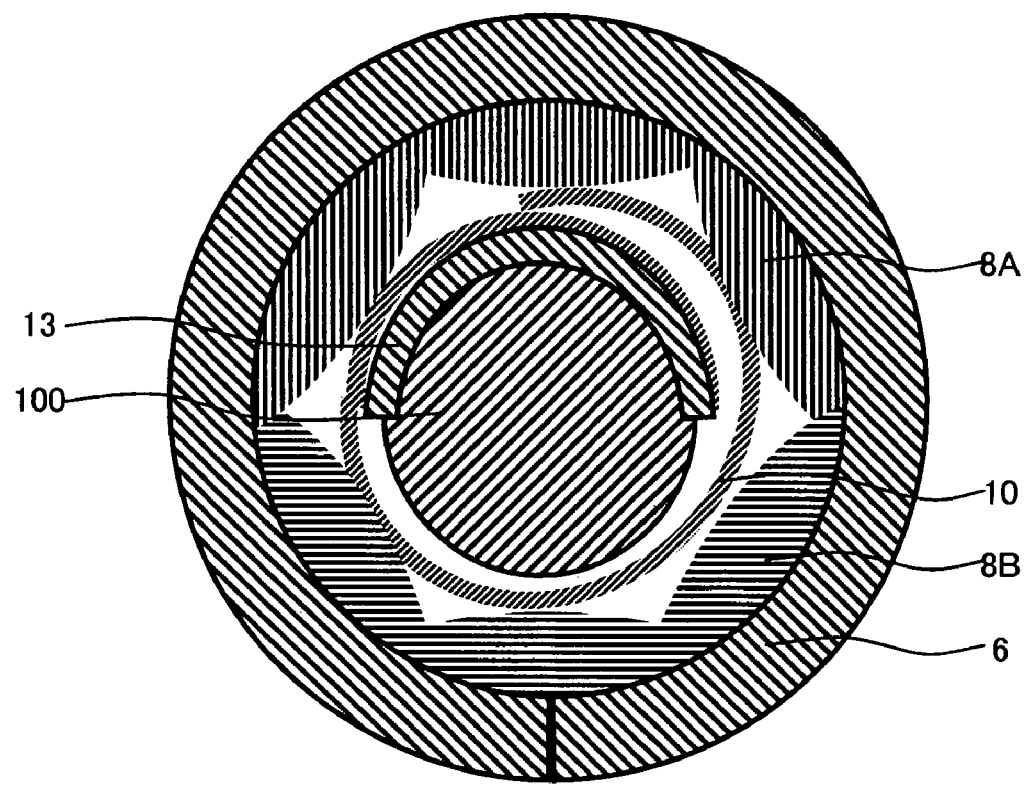
FIG. 3 is a sectional view for illustrating an internal structure of a measuring part 5 of the blood-pressure meter 1 according to the first embodiment.

Referring to FIG. 3, in measuring part 5, compressing and fixing air bladders 8A and 8B are included inside housing 6, and compressing and fixing air bladders 8A and 8B are inflated and contracted by compressing and fixing air systems 30A and 30B (see FIG. 4) respectively.

Curler 10 formed by a plate-shape member wound in the substantially cylindrical shape is disposed inside compressing and fixing air bladder 8, and curler 10 is elastically deformed in the radial direction by application of an external force. Measuring air bladder 13 is disposed inside curler 10, and is inflated and reduced by a measuring air system 20 (see FIG. 4) to be described later.

Figure 4:
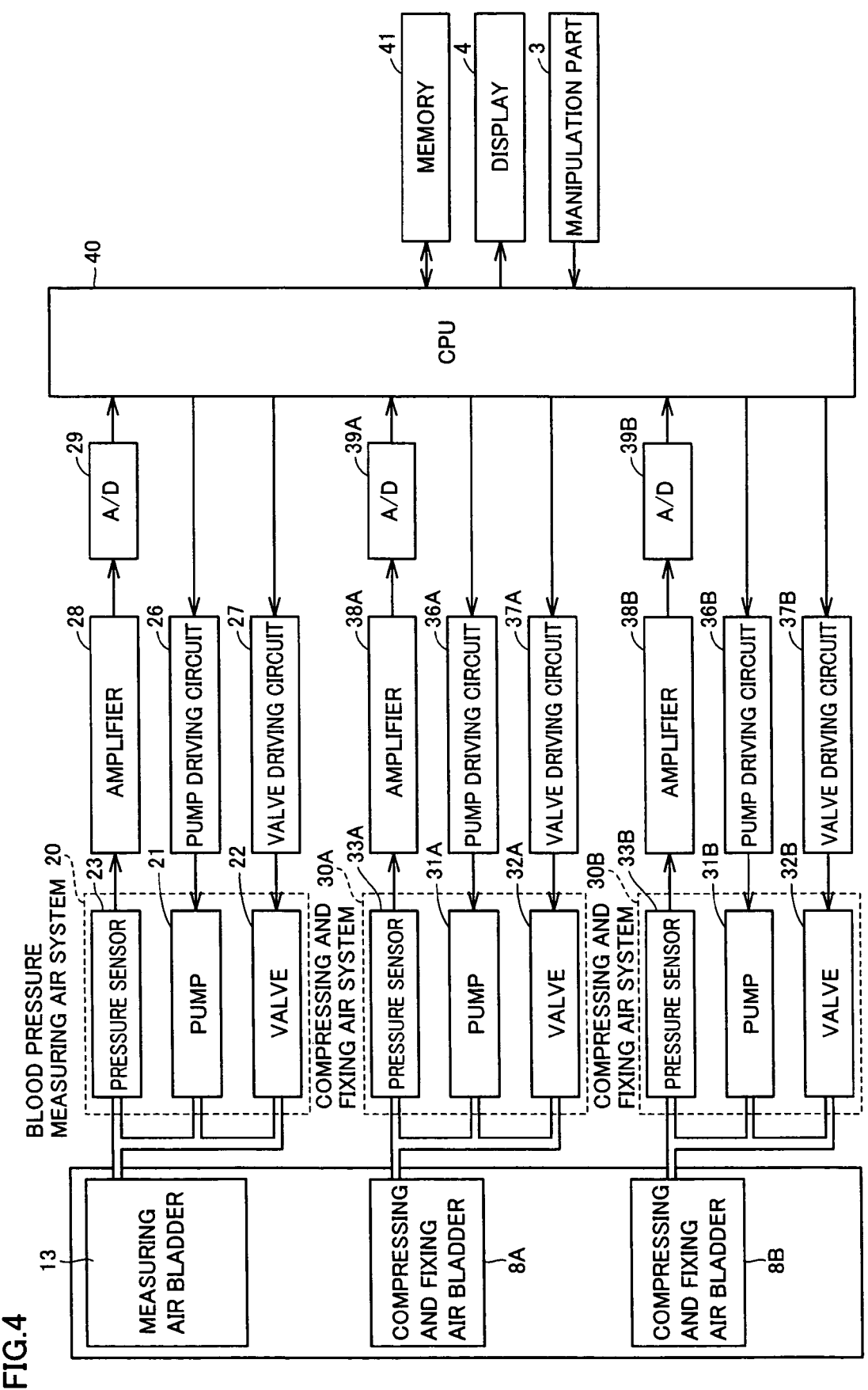
FIG. 4 is a block diagram showing a specific example of a functional configuration of the blood-pressure meter 1 according to the first embodiment.

Referring to FIG. 4, blood-pressure meter 1 includes measuring air bladder 13 and compressing and fixing air bladders 8A and 8B, and measuring air bladder 13 and compressing and fixing air bladders 8A and 8B are connected to a measuring air system 20 and compressing and fixing air systems 30A and 30B respectively. Measuring air system 20 includes a pressure sensor 23 measuring an internal pressure of measuring air bladder 13, a pump 21 supplying and discharging the air to and from measuring air bladder 13, and a valve 22. Compressing and fixing air systems 30A and 30B include pressure sensors 33A and 33B measuring the internal pressures of compressing and fixing air bladders 8A and 8B, pump 31A and 31B supplying and discharging the air to and from compressing and fixing air bladders 8A and 8B, and valves 32A and 32B respectively.

Blood-pressure meter 1 includes CPU (Central Processing Unit) 40 controlling the whole of blood-pressure meter 1, an amplifier 28 connected to measuring air system 20, a pump driving circuit 26, and a valve driving circuit 27, amplifiers 38A and 38B, pump driving circuits 36A and 36B, valve driving circuits 37A and 37B connected to compressing and fixing air bladders 8A and 8B respectively, A/D (Analog to Digital) converters 29, 39A, and 39B connected to amplifiers 28, 38A, and 38B respectively, a memory 41 in which a program executed by CPU 40 and the measurement result are stored, a display 4 displaying the measurement result, and a manipulation part 3 including a measurement start button, a measurement end button, and the like.

CPU 40 executes a predetermined program stored in memory 41 based on a manipulation signal inputted from manipulation part 3, and CPU 40 outputs a control signal to pump driving circuits 26, 36A and 36B and valve driving circuits 27, 37A and 37B. Pump driving circuits 26, 36A and 36B and valve driving circuits 27, 37A and 37B drive pumps 21, 31A and 31B and valves 22, 32A and 32B according to the control signal to perform the blood pressure measuring operation.

Pressure sensor 23 detects the internal pressure of measuring air bladder 13, and inputs a detection signal to amplifier 28. Pressure sensors 33A and 33B corresponding to the compression degree detection means detect the internal pressures of compressing and fixing air bladders 8A and 8B, and input the detection signal to amplifiers 38A and 38B. The internal pressures of compressing and fixing air bladders 8A and 8B correspond to the compression degree of the measuring fluid bladder compressed by the measuring fluid bladder compressing means. The inputted pressure signals are respectively amplified to predetermined amplitudes by amplifiers 28, 38A and 38B and converted into digital signals by A/D converters 29, 39A and 39B, and the digital signals are inputted to CPU 40.

CPU 40 performs a predetermined process based on the internal pressures of measuring air bladder 13 and compressing and fixing air bladders 8A and 8B which are obtained from pressure sensors 23, 33A and 33B, and CPU 40 outputs the control signal to pump driving circuits 26, 36A and 36B and valve driving circuits 27, 37A and 37B according to the process result. CPU 40 refers to a blood pressure value based on the internal pressure of measuring air bladder 13 obtained from pressure sensor 23, and outputs the measurement result to display the same on display 4.

Figure 5:
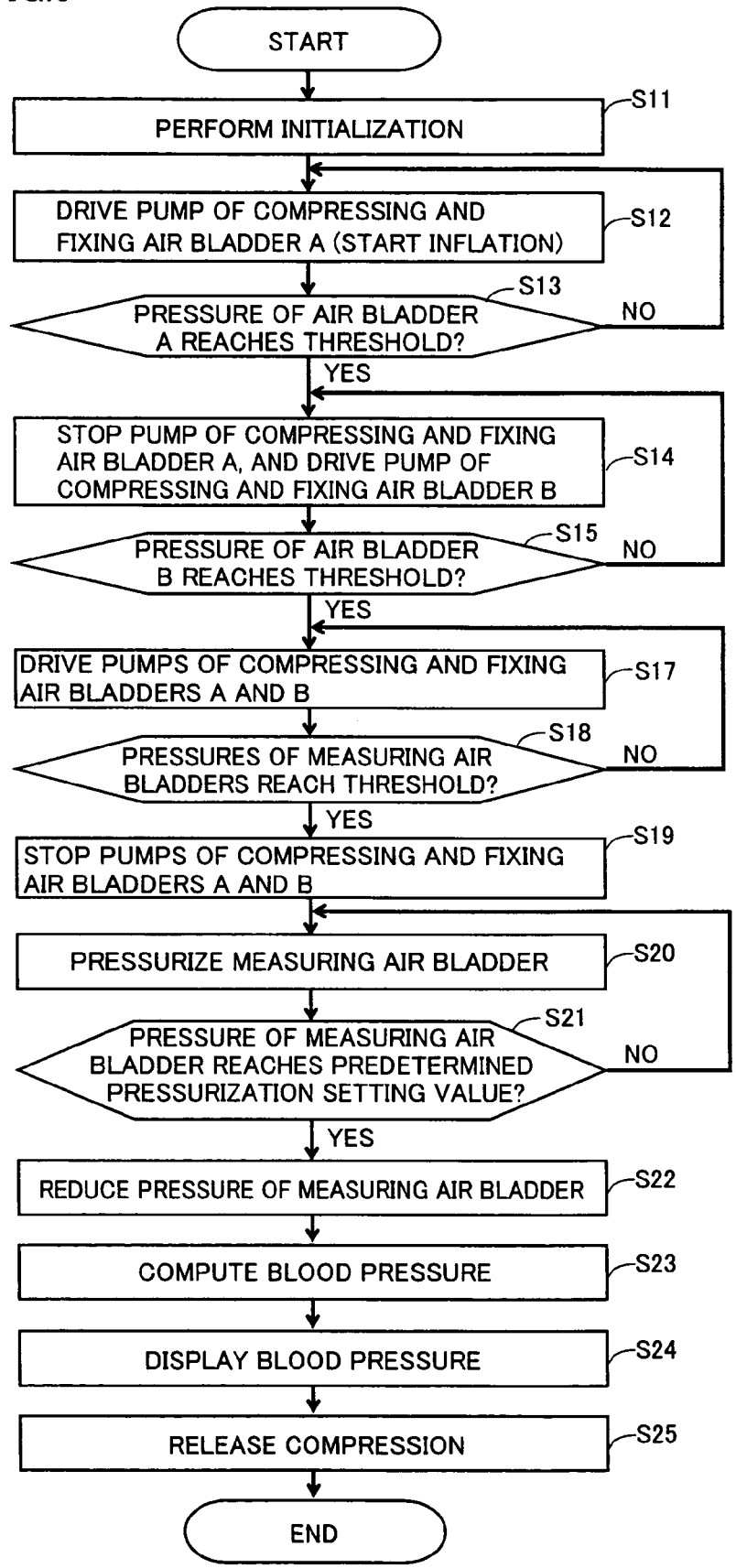
FIG. 5 is a flowchart showing a blood pressure measuring operation in the blood-pressure meter 1 according to the first embodiment.

CPU 40 reads and executes the program stored in memory 41, and controls each unit shown in FIG. 4, thereby realizing a blood pressure measuring operation shown in a flowchart of FIG. 5 performed by blood-pressure meter 1.

Referring to FIG. 5, in Step S11, initialization is performed such that a reference of the sensor is set to an atmospheric pressure, and then measuring air bladder 13 is preliminarily pressurized. In Step S12, CPU 40 outputs a control signal to pump driving circuit 36A and valve driving circuit 37A to drive pump driving circuit 36A and valve driving circuit 37A, and CPU 40 starts the pressurization of compressing and fixing air bladder 8A. CPU 40 monitors the internal pressure of compressing and fixing air bladder 8A obtained from pressure sensor 33A. When the internal pressure reaches a predetermined first threshold (YES in Step S13), CPU 40 outputs the control signal to pump driving circuit 36A and valve driving circuit 37A to stop the pressurization of compressing and fixing air bladder 8A in Step S14. CPU 40 further outputs the control signal to pump driving circuit 36B and valve driving circuit 37B to drive pump driving circuit 36B and valve driving circuit 37B, and CPU 40 starts the pressurization of compressing and fixing air bladder 8B.

When the pressurization of compressing and fixing air bladder 8B is started in Step S14, CPU 40 monitors the internal pressure of the compressing and fixing air bladder 8B. Compressing and fixing air bladder 8B is inflated and pressed to increase the internal pressure of compressing and fixing air bladder 8B. When the internal pressure of compressing and fixing air bladder 8B reaches a predetermined second threshold (YES in Step S15), CPU 40 outputs the control signal to pump driving circuit 36A and valve driving circuit 37A to drive pump driving circuit 36A and valve driving circuit 37A, and CPU 40 pressurizes both compressing and fixing air bladder 8B and compressing and fixing air bladder 8A in Step S17. Alternatively, CPU 40 monitors the internal pressure of compressing and fixing air bladder 8A instead of the internal pressure of compressing and fixing air bladder 8B in Step S15, and CPU 40 may output the control signal to pump driving circuit 36A and valve driving circuit 37A when the internal pressure of compressing and fixing air bladder 8A reaches the predetermined second threshold in Step S17.

During the pressurization of compressing and fixing air bladders 8A and 8B, CPU 40 monitors the internal pressure of measuring air bladder 13 and a change in internal pressure of measuring air bladder 13 obtained from pressure sensor 23. When these values reach predetermined values (YES in Step S18), CPU 40 ends the pressurization of compressing and fixing air bladders 8A and 8B in Step S19.

In Step S20, CPU 40 outputs the control signal to pump driving circuit 26 and valve driving circuit 27 to drive pump driving circuit 26 and valve driving circuit 27, and CPU 40 pressurizes measuring air bladder 13. When CPU 40 determines that the internal pressure of measuring air bladder 13 reaches a predetermined pressurization setting value (YES in Step S21), CPU 40 starts to depressurize measuring air bladder 13 in Step S22.

In Step S23, CPU 40 computes the blood pressure based on the internal pressure of measuring air bladder 13, which is obtained from pressure sensor 23 in pressurizing measuring air bladder 13 in Step S22. In Step S24, CPU 40 causes display 4 to display the blood pressure. In Step S25, the air in compressing and fixing air bladder 8 and the air in measuring air bladder 13 are vented to release the compression of the living body.

In the configuration of the present embodiment, the blood pressure is computed based on the internal pressure of measuring air bladder 13 obtained from pressure sensor 23 in depressurization. Alternatively, the blood pressure may be computed based on the internal pressure of measuring air bladder 13 obtained from pressure sensor 23 not in depressurization but in pressurization.

Figure 6:
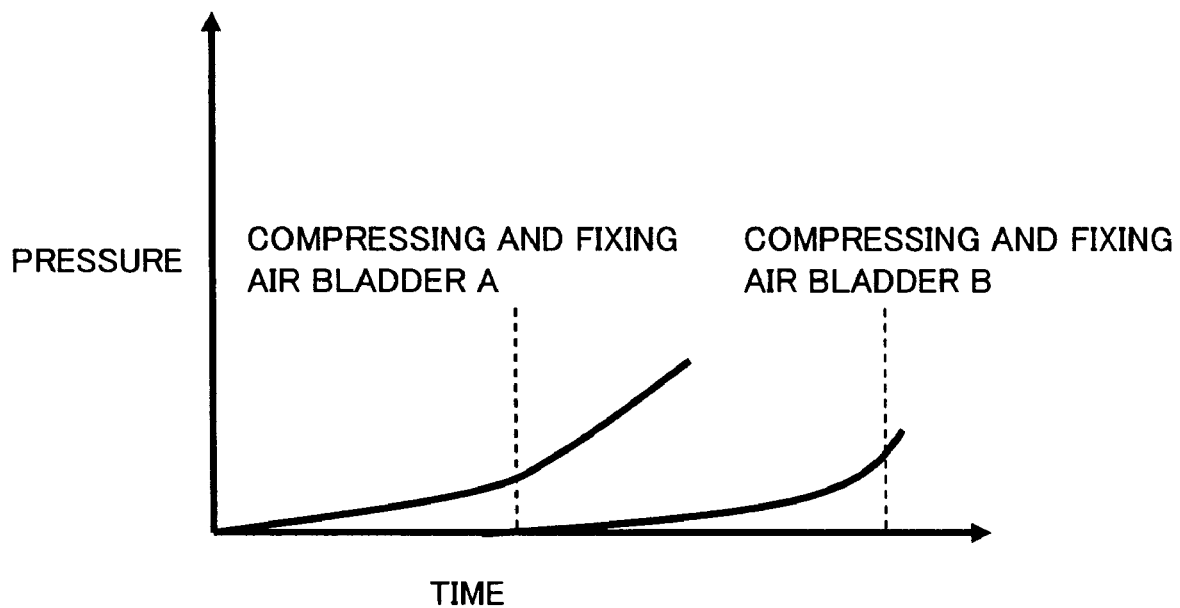
FIG. 6 is a view showing fluctuations in internal pressures of compressing and fixing air bladders 8A and 8B during the blood pressure measuring operation.

The above-described control is performed by blood-pressure meter 1 according to the first embodiment, thereby pressurizing the air bladder as shown in FIG. 6.

Referring to FIG. 6, when an instruction of operation start is provided, pump driving circuit 36A is driven to supply the air to compressing and fixing air bladder 8A, and the internal pressure is increased in Step S12. When the internal pressure of compressing and fixing air bladder 8A reaches the predetermined value (YES in Step S13), the drive of pump driving circuit 36A is stopped, and pump driving circuit 36B is driven to start the pressurization of compressing and fixing air bladder 8B in Step S14. Compressing and fixing air bladder 8A is compressed in association with the inflation of compressing and fixing air bladder 8B, thereby increasing the internal pressure of compressing and fixing air bladder 8A. That is, in blood-pressure meter 1 according to the first embodiment, in order to fix measuring air bladder 13 corresponding to the cuff to the living body, compressing and fixing air bladder 8A and compressing and fixing air bladder 8B exert different compression behaviors in pressurizing and inflating the compressing and fixing air bladders, compressing and fixing air bladder 8A compressing and fixing the measurement region from above is inflated, and then compressing and fixing air bladder 8B compressing and fixing the measurement region from below is inflated.

It is necessary that compressing and fixing air bladder 8 according to the first embodiment include at least two compressing and fixing air bladders arranged in the circumferential direction orthogonal to the artery of the upper arm. The compressing and fixing air bladders exert the different compression behaviors by separately controlling the supply/discharge of the air. However, the present invention is not limited to the configuration in which two compressing and fixing air bladders 8A and 8B are disposed. In the case where compressing and fixing air bladder 8 includes at least three compressing and fixing air bladders, CPU 40 performs the same control as described above. That is, CPU 40 separately drives the pump driving circuits to supply the air to the compressing and fixing air bladders, the compressing and fixing air bladder compressing and fixing the measurement region from above is inflated, and then the compressing and fixing air bladder compressing and fixing the measurement region from below is inflated. In the plurality of compressing and fixing air bladders, even some compressing and fixing air bladders may exert the same compression behavior, and CPU 40 may perform the control so as to cause at least the compressing and fixing air bladder compressing and fixing the measurement region from above to be inflated, and then to cause the compressing and fixing air bladder compressing and fixing the measurement region from below to be inflated.

Compressing and fixing air bladder 8 of blood-pressure meter 1 according to the first embodiment has the configuration in which CPU 40 drives the pump driving circuits in the above-described manner to exert the different compression behaviors. Therefore, the measuring air bladder corresponding to the cuff is compressed from above against the upper arm serving as the measurement region, and then the compressing and fixing air bladder located below is inflated. Accordingly, even in pressurizing the compressing and fixing air bladder, the upper arm is fixed to blood-pressure meter 1 to maintain the stable measurement attitude, so that the noise caused by the body movement can be prevented to improve the accuracy of blood pressure measurement.

Second Embodiment

Figure 7:
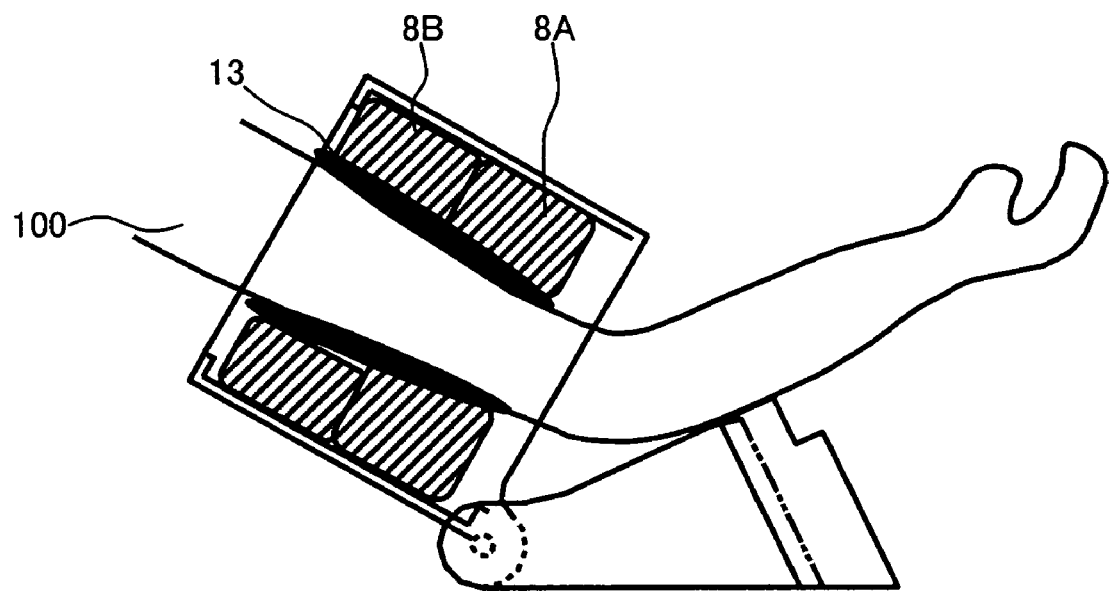
FIG. 7 is a schematic sectional view showing a state in which the blood pressure is measured using a blood-pressure meter 1 according to a second embodiment.

Referring to FIG. 7, similarly to blood-pressure meter 1 according to the first embodiment, in blood-pressure meter 1 according to a second embodiment, an upper arm 100 is inserted into housing 6 to place the elbow on the elbow holder, and the instruction of the measurement start is provided. Upper arm 100 is compressed and fixed by the living body compressing and fixing apparatus to measure the blood pressure.

In blood-pressure meter 1 according to the second embodiment, compressing and fixing air bladder 8 includes a plurality of compressing and fixing air bladders arranged in the length direction of the upper arm parallel to the artery of the upper arm, and the compressing and fixing air bladders exert different compression behaviors by separately controlling the supply/discharge of air. At this point, specifically it is assumed that compressing and fixing air bladder 8 includes two compressing and fixing air bladders 8A and 8B. When the upper arm is inserted into housing 6, compressing and fixing air bladder 8A is disposed along the circumference of the upper arm near a wrist while compressing and fixing air bladder 8B is disposed along the circumference of the upper arm far away from the wrist.

The functional configuration of blood-pressure meter 1 according to the second embodiment is similar to that of blood-pressure meter 1 according to the first embodiment shown in FIG. 4. The same blood pressure measuring operation as that of blood-pressure meter 1 according to the first embodiment shown in the flowchart of FIG. 5 is performed in the case where the blood pressure is measured using blood-pressure meter 1 according to the present embodiment.

As described above, the initialization is performed in Step S11, compressing and fixing air bladder 8A near the wrist is pressurized until the pressure reaches the first threshold in Steps S12 and S13, and the pressurization of compressing and fixing air bladder 8A is stopped to start the pressurization of compressing and fixing air bladder 8B in Step S14. When the internal pressure of compressing and fixing air bladder 8A or the internal pressure and the change in internal pressure of compressing and fixing air bladder 8B reach the second threshold, compressing and fixing air bladder 8A and compressing and fixing air bladder 8B are pressurized in Step S17.

In blood-pressure meter 1 according to the second embodiment, through the control of CPU 40, compressing and fixing air bladder 8A and compressing and fixing air bladder 8B exert the different compression behaviors when the compressing and fixing air bladders are pressurized and inflated to fix measuring air bladder 13 corresponding to the cuff to the living body. That is, the different pressurization is performed to compressing and fixing air bladder 8A near the wrist of the upper arm serving as the measurement region and compressing and fixing air bladder 8B far way from the wrist.

In the blood pressure measuring operation, the pressurization order of compressing and fixing air bladder 8A and compressing and fixing air bladder 8B is not limited, but compressing and fixing air bladder 8A is pressurized after compressing and fixing air bladder 8B is pressurized.

Similarly to the first embodiment, it is necessary that compressing and fixing air bladder 8 according to the second embodiment include at least the two compressing and fixing air bladders arranged in the length direction parallel to the artery of the upper arm. The compressing and fixing air bladders exert the different compression behaviors by separately controlling the supply/discharge of the air. However, the present invention is not limited to the configuration in which two compressing and fixing air bladders 8A and 8B are disposed. In the case where compressing and fixing air bladder 8 includes at least three compressing and fixing air bladders, CPU 40 performs the same control as described above. That is, CPU 40 separately drives the pump driving circuits to supply the air to the compressing and fixing air bladders, and CPU 40 separately inflates the compressing and fixing air bladders. In the plurality of compressing and fixing air bladders, even some compressing and fixing air bladders may exert the same compression behavior, and CPU 40 may control the inflation according to the circumference of the upper arm of the compressed measurement region.

Compressing and fixing air bladder 8 of blood-pressure meter 1 according to the second embodiment has the configuration in which CPU 40 drives the pump driving circuit to exert the different compression behaviors as described above. Therefore, the compressing and fixing air bladder can be inflated according to the shape of the upper arm serving as the measurement region. For example, even if the upper arm serving as the measurement region has the tapered shape, the measuring fluid bladder can properly be compressed and pressed against the measurement region according to the shape of the measurement region. Accordingly, the accuracy of blood pressure measurement can be enhanced.

Modification of First and Second Embodiments

Compressing and fixing air bladder 8 may include a plurality of compressing and fixing air bladders formed by a combination of the configuration of compressing and fixing air bladder 8 according to the first embodiment and the configuration of compressing and fixing air bladder 8 according to the second embodiment. The plurality of compressing and fixing air bladders exert the different compression behaviors by separately controlling the supply/discharge of the air, and the plurality of compressing and fixing air bladders are disposed in the direction orthogonal and/or parallel to the artery of the upper arm. Specifically, as shown in FIG. 8, compressing and fixing air bladder 8 may be formed by compressing and fixing air bladders 8A and 8B arranged in the length direction of the upper arm and compressing and fixing air bladder 8C disposed in the circumferential direction of the upper arm.

In blood-pressure meter 1 according to the modification, similarly CPU 40 separately controls pump driving circuits 36A, 36B, and 36C to pressurize compressing and fixing air bladders 8A, 8B, and 8C, and compressing and fixing air bladders 8A, 8B, and 8C are inflated with different compression behaviors. The control order is a control method formed by the combination of the control method according to the first embodiment and the control method according to the second embodiment. Specifically, compressing and fixing air bladders 8A and 8B compressing measuring air bladder 13 corresponding to the cuff from above the measurement region are pressurized until the internal pressures of compressing and fixing air bladders 8A and 8B reaches the thresholds respectively, and then compressing and fixing air bladder 8C compressing measuring air bladder 13 from below the measurement region is pressurized.

Figure 8:
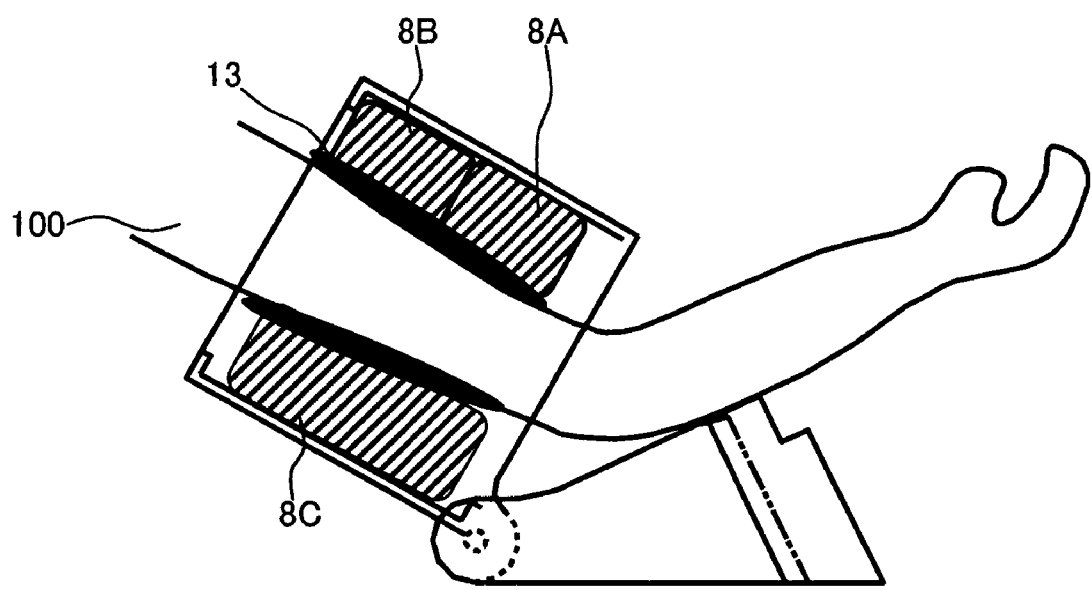
FIG. 8 is a schematic sectional view showing a state in which the blood pressure is measured using a blood-pressure meter 1 according to a modification of the first and second embodiments.

In the present modification, similarly to the above-described embodiments, the configuration of compressing and fixing air bladder 8 is not limited to the configuration shown in FIG. 8 as long as compressing and fixing air bladder 8 includes at least the two compressing and fixing air bladders, which are arranged in the direction orthogonal and/or parallel to the artery of the upper arm and exert the different compression behaviors by separately controlling the supply/discharge of the air.

Compressing and fixing air bladder 8 of blood-pressure meter 1 according to the modification has the above-described configuration, and CPU 40 drives the pump driving circuit to supply the air to compressing and fixing air bladder 8 as described above. Therefore, advantageously the upper arm is fixed to blood-pressure meter 1 to maintain the stable measurement attitude even in pressurizing the compressing and fixing air bladder. Additionally, even if the upper arm serving as the measurement region has the tapered shape, the measuring air bladders located at predetermined positions can be pressed with proper pressing forces according to the tapered shape. Accordingly, the accuracy of blood pressure measurement can be enhanced.

Third Embodiment

Figure 9:
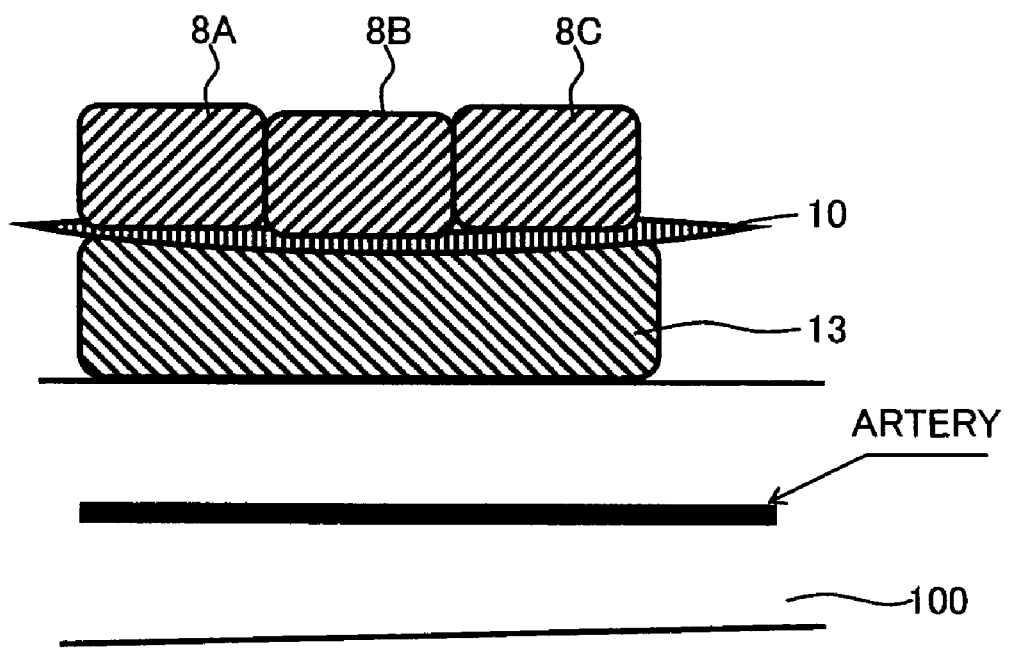
FIG. 9 is a view illustrating a configuration of a compressing and fixing air bladder 8 of a blood-pressure meter 1 according to a third embodiment and a positional relationship among the compressing and fixing air bladder 8, a curler 10, a measuring air bladder 13, and an upper arm.

In blood-pressure meter 1 according to a third embodiment, compressing and fixing air bladder 8 includes a plurality of compressing and fixing air bladders arranged in the length direction of the upper arm parallel to the artery of the upper arm, and the compressing and fixing air bladders exert different compression behaviors by separately controlling the supply/discharge of air. Referring to FIG. 9, it is assumed that compressing and fixing air bladder 8 includes three compressing and fixing air bladders 8A, 8B, and 8C. Compressing and fixing air bladders 8A, 8B, and 8C are sequentially disposed in the upper arm length direction from the shoulder toward the wrist. In compressing and fixing air bladders 8A, 8B, and 8C, compressing and fixing air bladder 8B located in the center is located in the center or the substantial center of measuring air bladder 13.

The functional configuration of blood-pressure meter 1 according to the third embodiment is substantially similar to that of blood-pressure meter 1 according to the first embodiment shown in FIG. 4. However, in addition to the configuration shown in FIG. 4, blood-pressure meter 1 according to the present embodiment further includes a configuration similar to the configuration for pressurizing and depressurizing compressing and fixing air bladders 8A and 8B. The configuration is connected to compressing and fixing air bladder 8C to control to pressurize and depressurize compressing and fixing air bladder 8C. That is, in addition to the configuration shown in FIG. 4, blood-pressure meter 1 further includes an amplifier 38C, a pump driving circuit 36C, a valve driving circuit 37C, and an A/D converter 39C. Amplifier 38C, pump driving circuit 36C, and valve driving circuit 37C are connected to compressing and fixing air bladder 8C. A/D converter 39C is connected to amplifier 38C.

Figure 10:
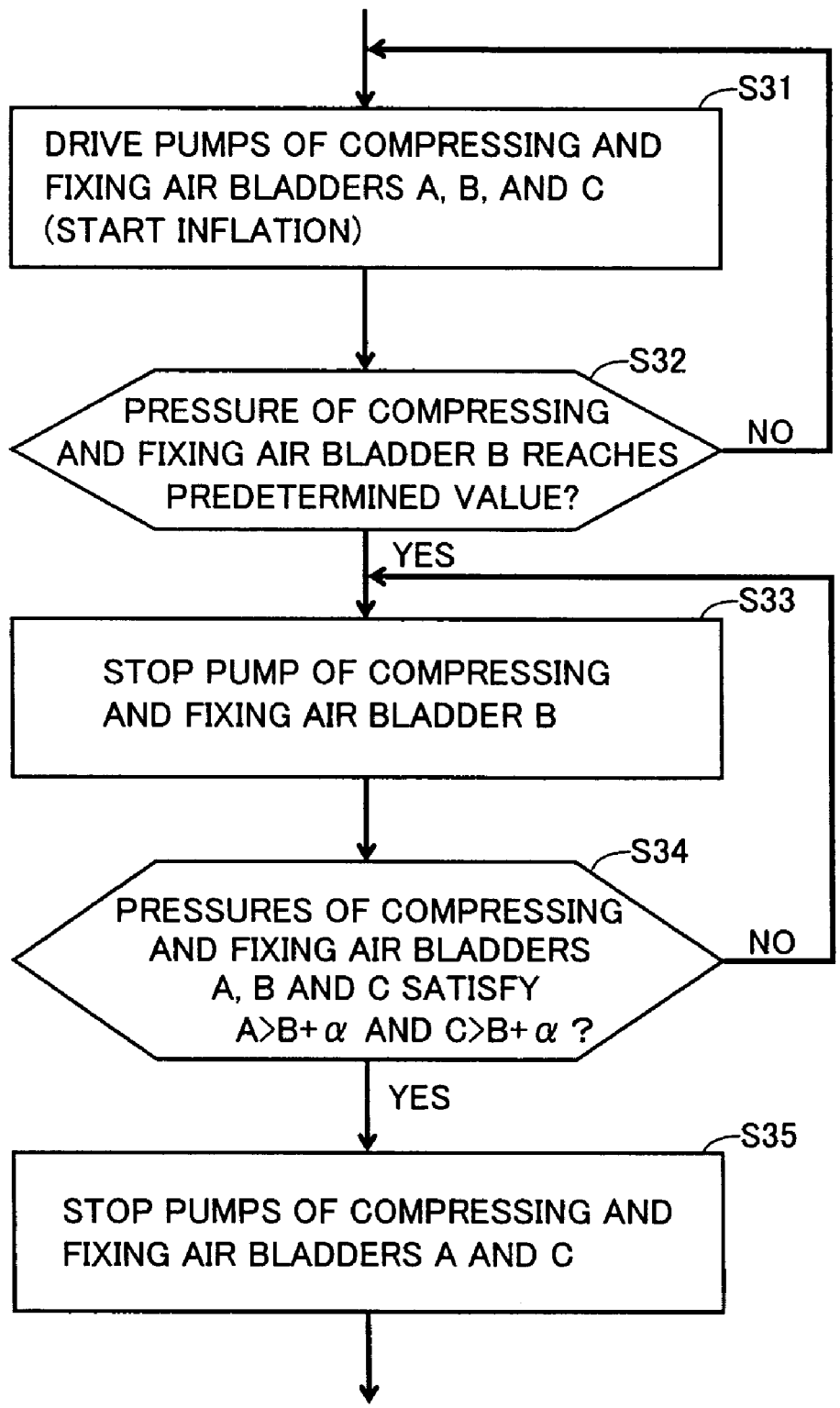
FIG. 10 is a flowchart showing an operation for inflating the compressing and fixing air bladder 8 in the blood pressure measuring operation performed by the blood-pressure meter 1 according to the third embodiment.

FIG. 10 is a flowchart showing operations corresponding to Steps S12 to S17 in the operations shown in the flowchart of FIG. 5. CPU 40 controls each unit by reading and executing the program stored in memory 41, thereby realizing the operations shown in the flowchart of FIG. 10.

Referring to FIG. 10, after the initialization is performed, CPU 40 outputs the control signal to pump driving circuits 36A, 36B, and 36C and valve driving circuits 37A, 37B, and 37C to drive pump driving circuits 36A, 36B, and 36C and valve driving circuits 37A, 37B, and 37C, and CPU 40 starts the pressurization of each of compressing and fixing air bladders 8A, 8B, and 8C in Step S31. CPU 40 monitors the internal pressures and the changes in internal pressures of compressing and fixing air bladder 8A, 8B, and 8C obtained from pressure sensors 33A, 33B, and 33C. When the internal pressure and the change in internal pressure of compressing and fixing air bladder 8B reach predetermined values (YES in Step S32), CPU 40 outputs the control signal to pump driving circuit 36B and valve driving circuit 37B to stop the pressurization of compressing and fixing air bladder 8B in Step S33.

CPU 40 further monitors the internal pressures and the changes in internal pressures of compressing and fixing air bladder 8A and 8C obtained from pressure sensors 33A and 33C. When the internal pressures and the changes in internal pressures of compressing and fixing air bladders 8A and 8C reach predetermined conditions (YES in Step S34), CPU 40 outputs the control signal to pump driving circuits 36A and 36C and valve driving circuits 37A and 37C to stop the pressurization of compressing and fixing air bladders 8A and 8C in Step S35. Then, the same operation as the blood pressure measuring operation according to the first embodiment is performed.

Assuming that A, B, and C are internal pressures of compressing and fixing air bladders 8A, 8B, and 8C respectively, the predetermined conditions include A>B+α and C>B+α. Where α is a constant satisfying α>0, and the constant α is previously stored in memory 41. Alternatively, a plurality of constants α are stored in memory 41, and a proper constant α may be selected and set according to measurement conditions such as the circumference of the upper arm and an air amount supplied to compressing and fixing air bladder 8.

The configuration of compressing and fixing air bladder 8 according to the third embodiment is not limited the configuration including three compressing and fixing air bladders 8A, 8B, and 8C as long as compressing and fixing air bladder 8 includes a plurality of compressing and fixing air bladders, which are arranged in the upper arm length direction parallel to the artery of the upper arm and exert the different compression behaviors by separately controlling the supply/discharge of the air. In the case where compressing and fixing air bladder 8 includes at least four compressing and fixing air bladders, CPU 40 performs the control similar to that described above. That is, CPU 40 separately drives the pump driving circuits to supply the air to the compressing and fixing air bladders, and CPU 40 separately inflates the compressing and fixing air bladders such that the internal pressure of the compressing and fixing air bladder located at the position corresponding to the position far way from the center of measuring air bladder 13 is higher than the internal pressure of the compressing and fixing air bladder located in the center or the substantial center of measuring air bladder 13. Alternatively, in the case where compressing and fixing air bladder 8 includes at least four compressing and fixing air bladders, CPU 40 may inflate the compressing and fixing air bladders according to the positions of the compressing and fixing air bladders such that the internal pressure becomes higher as the compressing and fixing air bladder is located at the position corresponding to the position farther way from the center of measuring air bladder 13. As described above with reference to the flowchart, in the plurality of compressing and fixing air bladders, some compressing and fixing air bladders may exert the same compression behavior. For example, the compressing and fixing air bladders located symmetrically or substantially symmetrically in relation to the position corresponding to the center of measuring air bladder 13 may exert the same compression behavior.

Figure 14:
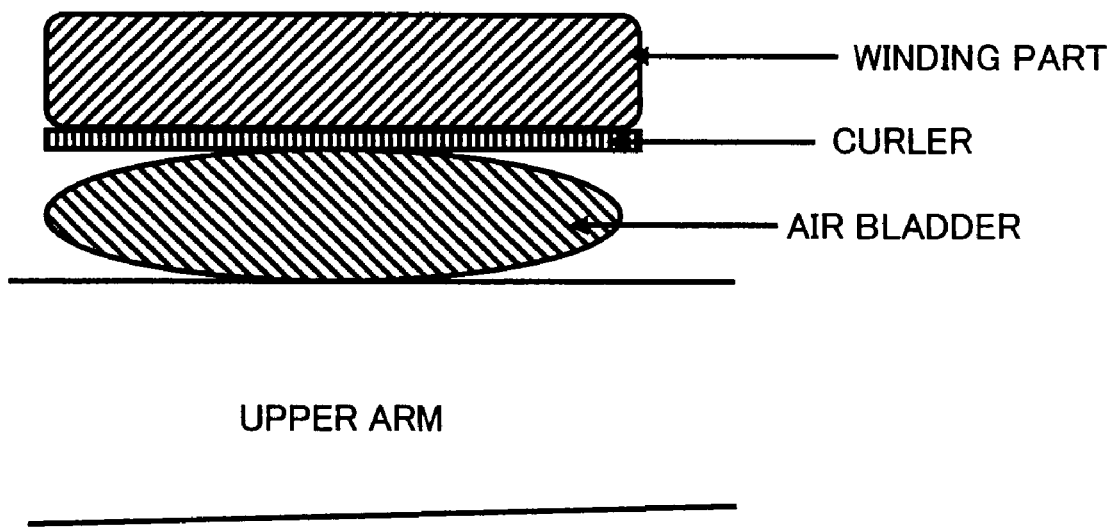
FIG. 14 is a view illustrating compression of a measuring fluid bladder.

Compressing and fixing air bladder 8 of blood-pressure meter 1 according to the third embodiment has the configuration in which CPU 40 drives the pump driving circuits in the above-described manner to exert the different compression behaviors. CPU 40 controls the pressurization of each compressing and fixing air bladder 8 as described above, and the compressing and fixing air bladder located farther way from the center of measuring air bladder 13 is pressed against the measurement region compared with the compressing and fixing air bladder located in the center or the substantial center of measuring air bladder 13. Therefore, the situation in which the pressing force does not act on the portion located away from the center of the measuring air bladder as described with reference to FIG. 14 can be prevented, and the artery is properly pressed over the necessary range by the measuring air bladder. Accordingly, the accuracy of blood pressure measurement can be improved.

[First Modification]

Figure 11A:
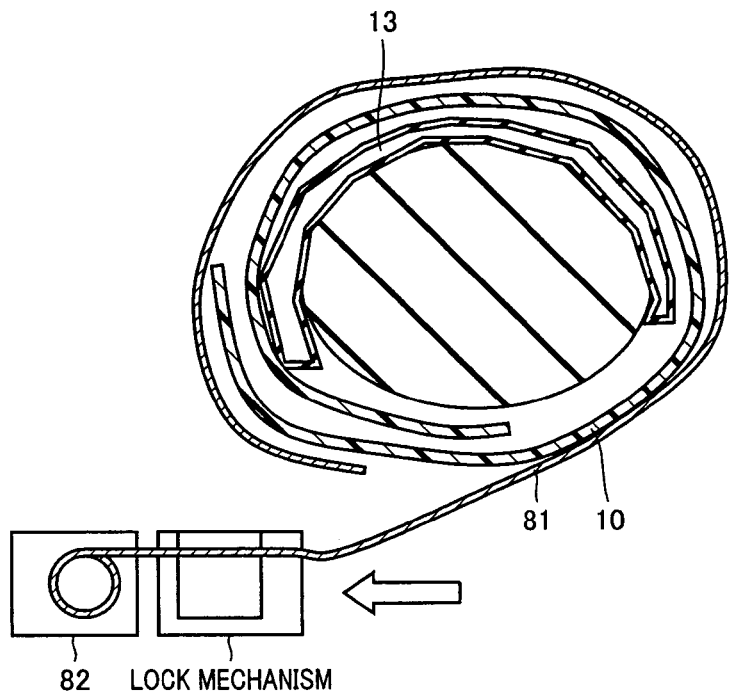
FIG. 11A is a view illustrating a mechanism of measuring fluid bladder compressing means included in a blood-pressure meter 1 according to a first modification.
Figure 11B:
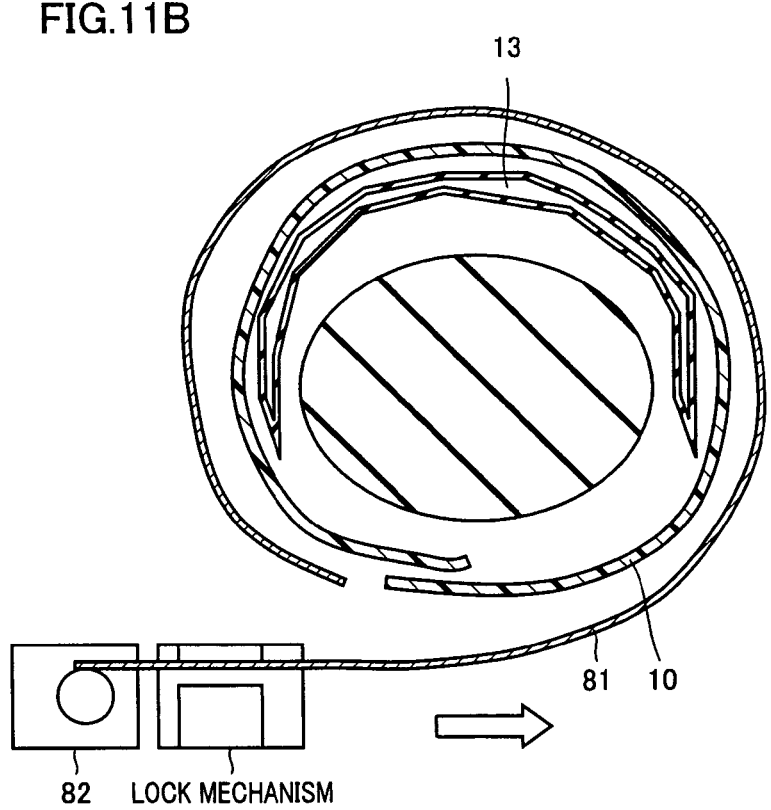
FIG. 11B is a view illustrating the mechanism of the measuring fluid bladder compressing means included in the blood-pressure meter 1 according to the first modification.

The measuring fluid bladder compressing means for compressing measuring air bladder 13 through curler 10 is not limited to the compressing and fixing air bladder, but any mechanism may be used as the measuring fluid bladder compressing means as long as the mechanism includes the same function. Specifically, as shown in FIGS. 11A and 11B, a first modification of blood-pressure meter 1 may include a wire 81 and a wire wind-up part 82 instead of compressing and fixing air bladder 8. Wire 81 compresses measuring air bladder 13 through curler 10, and wire wind-up part 82 is a mechanism driving a wire wind-up driving circuit (not shown) corresponding to pump driving circuit 36 to wind up wire 81. Measuring air bladder 13 is pressed against the measurement region through curler 10 by wire 81 wound up by wire wind-up part 82 as shown in FIG. 11A or by tightening delivered wire 81 with wire wind-up part 82 as shown in FIG. 11B. In the case where the measuring fluid bladder compressing means has the configuration shown in FIG. 11, CPU 40 outputs the control signal to the wire wind-up driving circuit to drive the wire wind-up driving circuit, and CPU 40 controls the pressing of measuring air bladder 13 by causing wire wind-up part 82 to wind up and deliver wire 81.

In blood-pressure meters 1 according to the second and third embodiments, a plurality of wires 81 are provided in the upper arm length direction, and the wire wind-up driving circuits are separately controlled, whereby the plurality of wires 81 exert the different compression behaviors. CPU 41 performs the same control, whereby wire 81 can be wound up and delivered according to the shape of the upper arm serving as the measurement region. For example, even if the upper arm serving as the measurement region has the tapered shape, the measuring air bladders located predetermined positions can properly be pressed against the measurement region according to the tapered shape. Accordingly, the accuracy of blood pressure measurement can be improved.

The compressing and fixing air bladder located farther way from the center of measuring air bladder 13 is pressed against the measurement region compared with the compressing and fixing air bladder located in the center or the substantial center of measuring air bladder 13. Therefore, the artery is properly pressed over the necessary range by the measuring air bladder, so that the accuracy of blood pressure measurement can be improved.

Compressing means in which an elastic material such as a spring and rubber inwardly disposed from housing 6 to curler 10 is utilized and mechanically compressing means inwardly disposed from housing 6 to curler 10 can be cited as another example of the measuring fluid bladder compressing means. In blood-pressure meter 1 according to the first embodiment includes the plurality of compressing means, which exert the different compression behaviors by separately controlling the compressing force and is disposed in the circumferential direction of the upper arm orthogonal to the artery of the upper arm. CPU 40 performs the same control to the compression of the compressing means. Therefore, the measuring air bladder corresponding to the cuff is pressed from above against the measurement region of the upper arm serving as the measurement region, and then the measuring air bladder can be pressed upward against the measurement region by the compressing means located below. Accordingly, the stable measurement attitude is maintained during the measurement to improve the accuracy of blood pressure measurement.

[Second Modification]

In each of the above-described embodiments, the measuring fluid bladder compressing means corresponding to compressing and fixing air bladders 8A to 8C includes a plurality of components (such as the compressing and fixing air bladder and the wire), and CPU 40 separately controls the compression of the measuring fluid bladder compressing means to exert the different compression behaviors. The configuration of the measuring fluid bladder compressing means is not limited to the configuration, but the measuring fluid bladder compressing means may be formed by one or a plurality of components to exert the different compression behaviors due to a difference in characteristic.

Figure 12:
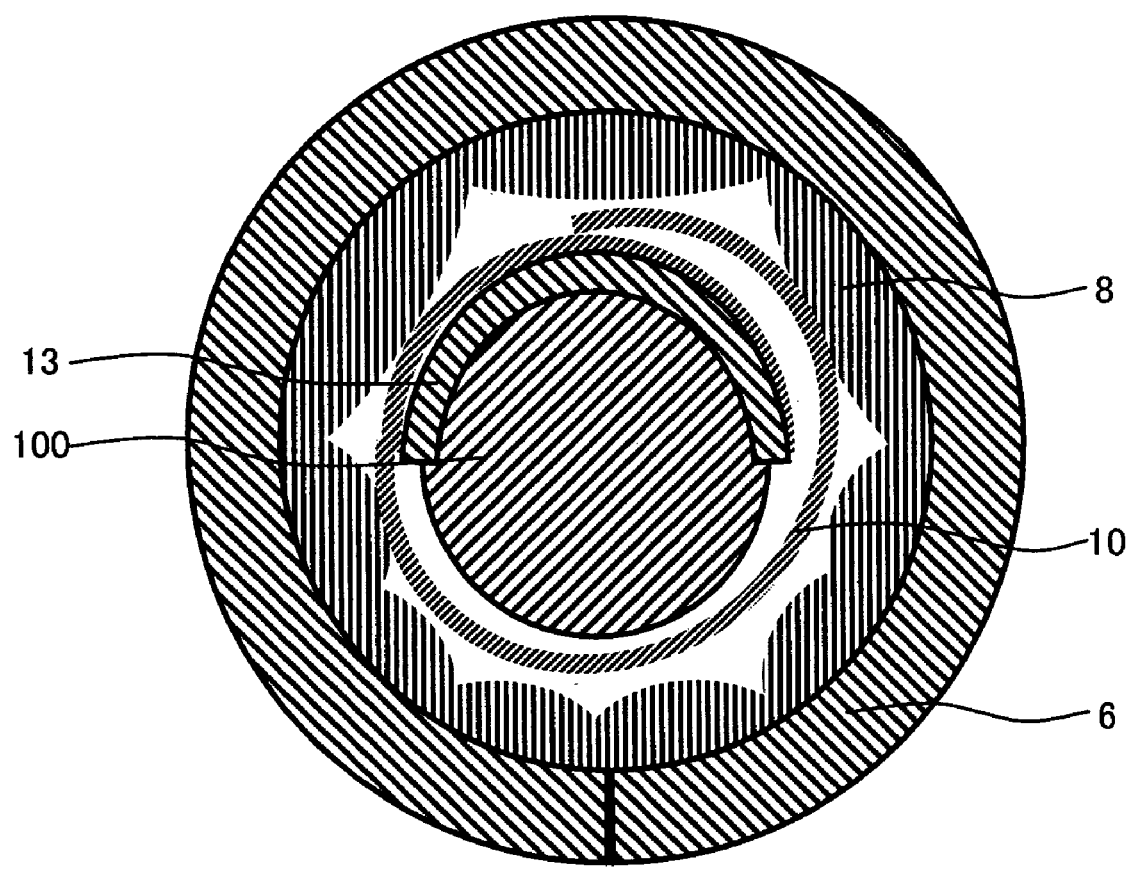
FIG. 12 is a view illustrating a configuration of a measuring air bladder 8 included in a blood-pressure meter 1 according to a second modification.
Figure 13A:
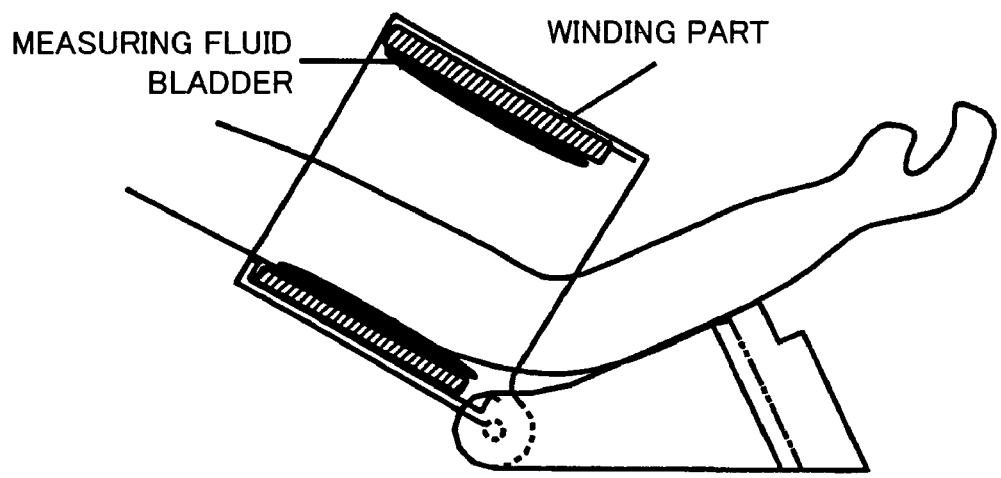
FIG. 13A is a schematic view illustrating fixing of a cuff in a blood-pressure meter having a configuration in which two fluid bladders independently provided through a curler are used in both winding of the cuff and blood pressure measurement.
Figure 13B:
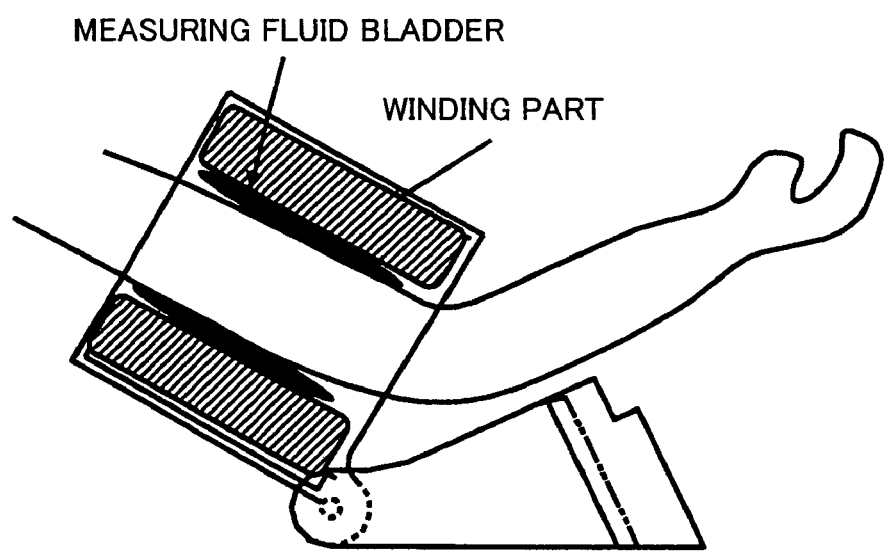
FIG. 13B is a schematic view illustrating the fixing of the cuff when the blood pressure measurement is performed using the blood-pressure meter having the configuration in which the two fluid bladders independently provided through the curler are used in both winding of the cuff and blood pressure measurement.

Specifically, referring to FIG. 12, in blood-pressure meter 1 according to a second modification, compressing and fixing air bladder 8 is formed by a single component, and the upper portion and lower portion of compressing and fixing air bladder 8 differ from each other in the number of seams per unit area of the measurement region of the air bladder. The seam of the air bladder decreases an inflation stroke.

The seam portion becomes a node of compressing and fixing air bladder 8 to restrict the stroke toward the direction of measuring air bladder 13. As shown in FIG. 12, when the number of seams of the lower portion of the measurement region is increased compared with the upper portion of the measurement region, the stroke toward the direction of measuring air bladder 13 located in the lower portion is decreased compared with the stroke toward the direction of measuring air bladder 13 of compressing and fixing air bladder 8 located in the upper portion. Therefore, the same effect as in the second embodiment can be obtained.

In blood-pressure meter 1 according to the second modification, when the air is supplied to compressing and fixing air bladder 8, the inflation stroke is decreased by the seam. Therefore, the upper portion and lower portion of the measurement region differ from each other in the inflation stroke, and the different compression behaviors are exerted to measuring air bladder 13.

Specifically, instead of the configuration of compressing and fixing air bladder 8 including the plurality of measuring air bladders disposed in the upper arm circumferential direction orthogonal to the artery of the upper arm in blood-pressure meter 1 according to the first embodiment, blood-pressure meter 1 according to the second modification includes compressing and fixing air bladder 8 having the configuration in which the number of seams is changed in the upper arm circumferential direction orthogonal to the artery of the upper arm. Therefore, the compression behavior of compressing and fixing air bladder 8 from above the measuring air bladder can differ from the compression behavior of compressing and fixing air bladder 8 from below the measuring air bladder.

Similarly, instead of the configuration of compressing and fixing air bladder 8 including a plurality of measuring air bladders disposed in the length direction parallel to the artery of the upper arm in blood-pressure meters 1 according to the second and third embodiments, blood-pressure meter 1 according to the second modification includes compressing and fixing air bladder 8 having the configuration in which the number of seams per unit area of the measurement region of the air bladder is changed in the direction parallel to the artery of the upper arm. Therefore, the compression behavior of compressing and fixing air bladder 8 to the measuring air bladder can be changed in the direction parallel to the artery of the upper arm.

In addition to the number of seams per unit area of the measurement region of the air bladder, the same function can be exhibited even if a material, the shape such as a thickness, and surface frictional resistance are used as the characteristic of the measuring fluid bladder compressing means.

It is to be understood that the above embodiments are disclosed only by way of example and the present invention is not limited to the above embodiments. The scope of the present invention is shown by not the above description but by claims, and it is intended that meanings equivalent to claims and all changes within claims are also included.

The invention claimed is:

1. A blood pressure measuring apparatus comprising:
a measuring fluid bladder;
a first supply part to supply a fluid to said measuring fluid bladder;
a sensor to measure an internal pressure of said measuring fluid bladder;
a measuring fluid bladder compressing part to compress said measuring fluid bladder in a measurement region direction; and
a compression degree detector to measure a degree of said measuring fluid bladder compressed by said measuring fluid bladder compressing part, wherein
said measuring fluid bladder compressing part includes:
a first compressing part comprising a first air bladder and a first air system and configured to compress said measuring fluid bladder while exerting a first compression behavior; and
a second compressing part comprising a second air bladder and a second air system and configured to compress said measuring fluid bladder while exerting a second compression behavior.

2. The blood pressure measuring apparatus according to claim 1, further comprising a controller to control compression of said measuring fluid bladder in said measuring fluid bladder compressing part, wherein
said controller controls such that said first compressing part is compressed using said measuring fluid bladder while exerting said first compression behavior, and said controller controls such that said second compressing part is compressed using said measuring fluid bladder while exerting said second compression behavior.

3. The blood pressure measuring apparatus according to claim 2, wherein said controller controls compression in said measuring fluid bladder compressing part based on an internal pressure of said measuring fluid bladder, information indicating a change in internal pressure of said measuring fluid bladder, and said compression degree of said measuring fluid bladder compressing part.

4. The blood pressure measuring apparatus according to claim 2, wherein said measuring fluid bladder compressing part is a compressing fluid bladder,
said measuring fluid bladder compressing part further includes:
a second supply part to supply a fluid to a first compressing fluid bladder functioning as said first compressing part; and
a third supply part to supply a fluid to a second compressing fluid bladder functioning as said second compressing part, and said controller controls the fluid supply in said second supply part and said third supply part to control compression in said measuring fluid bladder compressing part.

5. The blood pressure measuring apparatus according to claim 2, wherein said measurement region is an upper arm, said first compressing part and said second compressing part are disposed orthogonal to an artery of the upper arm with said measuring fluid bladder adapted to be attached to said upper arm, and said first compressing part is disposed at a position where said measuring fluid bladder located above said upper arm is compressed from above toward said upper arm while said second compressing part is disposed at a position where said measuring fluid bladder located below said upper arm is compressed from below toward said upper arm, and said controller performs control such that said first compressing part compresses said measuring fluid bladder and then said second compressing part compresses said measuring fluid bladder.

6. The blood pressure measuring apparatus according to claim 2, wherein said measurement region is an upper arm, and said first compressing part and said second compressing part are disposed in parallel with an artery of the upper arm with said measuring fluid bladder adapted to be attached to said upper arm, and said first compressing part is disposed at a position close to a shoulder on an upstream of said upper arm while said second compressing part is disposed at a position close to a wrist on a downstream side of said upper arm.

7. The blood pressure measuring apparatus according to claim 6, wherein said controller performs control such that a compression degree in said second compressing part is larger than a compression degree in said first compressing part.

8. The blood pressure measuring apparatus according to claim 2, wherein said measurement region is an upper arm, said first compressing part and said second compressing part are disposed in parallel with an artery of the upper arm with said measuring fluid bladder adapted to be attached to said upper arm, and said first compressing part is disposed in a substantial center in a direction parallel to said artery of said measuring fluid bladder while said second compressing part is disposed at a position closer to an end rather than the center in the direction parallel to said artery of said measuring fluid bladder, and said controller performs control such that a compression degree in said second compressing part is larger than a compression degree in said first compressing part.

9. The blood pressure measuring apparatus according to claim 1, wherein said first compressing part is a part corresponding to a first characteristic in said measuring fluid bladder compressing part, and said first compressing part exerts said first compression behavior according to said first characteristic, and said second compressing part is a part corresponding to a second characteristic in said measuring fluid bladder compressing part, and said second compressing part exerts said second compression behavior according to said second characteristic.

10. The blood pressure measuring apparatus according to claim 9, wherein said measuring fluid bladder compressing part is a compressing fluid bladder, and said first characteristic and said second characteristic are the number of seams of said compressing fluid bladder.

11. The blood pressure measuring apparatus according to claim 1, wherein each of said air systems includes a pump configured to supply and discharge air to and from a corresponding air bladder and a pressure sensor configured to measure an internal pressure of a corresponding air bladder.

12. The blood pressure measuring apparatus according to claim 1, wherein said first and second compression behaviors differ by separately controlling a supply and discharge of air to and from said first and second compressing parts.

* * * * *